United States Patent
Zhang et al.

(10) Patent No.: US 12,274,480 B2
(45) Date of Patent: Apr. 15, 2025

(54) VERTEBRAL BODY DISTRACTION SUPPORT NAIL

(71) Applicant: THE FOURTH MEDICAL CENTER OF THE GENERAL HOSPITAL OF THE CHINESE PEOPLE'S LIBERATION ARMY, Beijing (CN)

(72) Inventors: Wei Zhang, Beijing (CN); Zhongyang Liu, Beijing (CN); Jiantao Li, Beijing (CN); Chuyang Zeng, Beijing (CN); Xiaomeng Ren, Beijing (CN); Peifu Tang, Beijing (CN)

( * ) Notice: Subject to any disclaimer, the term of this patent is extended or adjusted under 35 U.S.C. 154(b) by 0 days.

(21) Appl. No.: 17/907,255

(22) PCT Filed: Sep. 6, 2022

(86) PCT No.: PCT/CN2022/117182
§ 371 (c)(1),
(2) Date: Sep. 23, 2022

(87) PCT Pub. No.: WO2023/245877
PCT Pub. Date: Dec. 28, 2023

(65) Prior Publication Data
US 2024/0293158 A1    Sep. 5, 2024

(30) Foreign Application Priority Data
Jun. 23, 2022 (CN) .......................... 202210719398.9
Jun. 23, 2022 (CN) .......................... 202221587735.5

(51) Int. Cl.
*A61B 17/88* (2006.01)
*A61B 17/70* (2006.01)
*A61F 2/46* (2006.01)
*A61B 17/68* (2006.01)

(52) U.S. Cl.
CPC ...... *A61B 17/8858* (2013.01); *A61B 17/7076* (2013.01); *A61F 2/4611* (2013.01); *A61B 2017/681* (2013.01)

(58) Field of Classification Search
CPC ............ A61B 17/8855; A61B 17/8858; A61B 17/7076
See application file for complete search history.

(56) References Cited

U.S. PATENT DOCUMENTS

2014/0100581 A1* 4/2014 Reimels ............. A61B 17/8858
606/99

* cited by examiner

*Primary Examiner* — Olivia C Chang
(74) *Attorney, Agent, or Firm* — Novoclaims Patent Services LLC; Mei Lin Wong

(57) ABSTRACT

A vertebral body distraction support nail, including a support nail body including an inner core, an outer sleeve and a distraction ball, and a support nail cap including a cylindrical upper support nail cap and a pressure cap. The inner core is threadedly connected inside the outer sleeve, and has upper and lower ends both extending out of the outer sleeve. The lower end of the inner core is provided with a tapered stapling head. The distraction ball is fitted over the inner core between the tapered stapling head and the outer sleeve. An upper support nail cap cavity has a lower end connected to an upper end of the outer sleeve and an upper end into which the upper end of the inner core extends. The pressure cap is engaged with and slidably connected to the upper end of the inner core and the upper support nail cap.

18 Claims, 16 Drawing Sheets

VERTEBRAL BODY DISTRACTION SUPPORT NAIL

The present invention claims the priority of the applications, filed by the applicant, with the application date of Jun. 23, 2022 and the application No. CN202210719398.9, and entitled "VERTEBRAL BODY DISTRACTION SUPPORT NAIL", and with the application date of Jun. 23, 2022 the application No. CN202221587735.5, and entitled "VERTEBRAL BODY DISTRACTION SUPPORT NAIL", respectively, which are incorporated herein by reference in their entirety.

TECHNICAL FIELD

The present invention relates to a medical instrument, and in particular, to a vertebral body distraction support nail.

BACKGROUND

For patients suffered from lumbar spine burst fractures, a fixation and reduction mechanism of a pedicle screw rod system is to reduce a fractured vertebral body through indirect pulling. The periphery of the fractured vertebral body can be effectively reduced under the pulling of the annulus fibrosus of the intervertebral disc. However, the central bony block of the anterior middle column cannot be pulled and reduced, thereby causing central collapse loss, and resulting in insufficient reduction. Moreover, a cavity is formed in the reduced vertebral body, thereby causing insufficiency of anterior support, further long-term height loss of the vertebral body, and even degeneration of the intervertebral discs at adjacent segments. Some patients even have aggravated kyphosis, residual waist and back pain, or even an internal fixation failure.

SUMMARY

The technical problem to be solved by the present invention is to provide a vertebral body distraction support nail, which can distract a collapsed bony block from the inside of a fractured vertebral body, so that the fractured vertebral body is reduced well, and occurrence of long-term complications is reduced.

The vertebral body distraction support nail of the present invention includes a support nail body and a support nail cap. The support nail body includes an inner core, an outer sleeve and a distraction ball. The inner core is threadedly connected inside the outer sleeve. An upper end and a lower end of the inner core both extend to the outside of the outer sleeve. The lower end of the inner core is provided with a tapered stapling head. The distraction ball is fitted over the inner core between the tapered stapling head and the outer sleeve. The support nail cap includes an upper support nail cap and a pressure cap. The upper support nail cap is of a cylindrical structure. A lower end of a cavity of the upper support nail cap is connected to an upper end of the outer sleeve. The upper end of the inner core extends to an upper end of the cavity of the upper support nail cap. The pressure cap is engaged with and slidably connected to the upper end of the inner core. The pressure cap is engaged with and slidably connected to the upper support nail cap. The pressure cap slides along the inner core and the upper support nail cap in an axial direction. When the pressure cap slides up along the axial direction of the upper support nail cap and releases the engagement and slidable connection with the upper support nail cap, the pressure cap still keeps the engagement and slidable connection with the inner core. When the tapered stapling head moves close to the lower end of the outer sleeve, the distraction ball performs distraction.

According to the vertebral body distraction support nail of the present invention, the distraction ball includes an upper sleeve ring and a lower sleeve ring. The upper sleeve ring and the lower sleeve ring are both fitted over the inner core between the tapered stapling head and the lower end of the outer sleeve. The upper sleeve ring abuts against the lower end of the outer sleeve. The lower sleeve ring abuts against an upper end of the tapered stapling head. A plurality of distraction pieces are fixedly connected between the upper sleeve ring and the lower sleeve ring. The plurality of distraction pieces are arranged around the circumference of the inner core. When the tapered stapling head moves close to the lower end of the outer sleeve, the distraction pieces bulge and deform away from the inner core.

According to the vertebral body distraction support nail of the present invention, two first lugs are fixedly connected on the upper support nail cap, and two second lugs are fixedly connected on the pressure cap.

According to the vertebral body distraction support nail of the present invention, the upper support nail cap includes an upper cylinder and a lower cylinder which are integrally formed. An inner cylinder diameter of the upper cylinder is greater than an inner cylinder diameter of the lower cylinder. The upper end of the outer sleeve is of a hollow prismatic structure. A lower part of a cavity of the lower cylinder is a prism mating with the upper end of the outer sleeve. An upper part of the cavity of the lower cylinder is provided with a first stop step. The lower part of the cavity of the lower cylinder is fitted over the upper end of the outer sleeve. The upper end of the outer sleeve abuts against the first stop step. The upper end of the inner core passes through the cavity of the lower cylinder and extends into a cavity of the upper cylinder.

According to the vertebral body distraction support nail of the present invention, the upper support nail cap includes an upper cylinder and a lower cylinder which are integrally formed. An inner cylinder diameter of the upper cylinder is greater than an inner cylinder diameter of the lower cylinder. An outer side wall of the upper end of the outer sleeve is provided with sliders. A lower part of a cavity of the lower cylinder is provided with sliding slots arranged axially. An upper part of the cavity of the lower cylinder is provided with a first stop step. The lower part of the cavity of the lower cylinder is fitted over the upper end of the outer sleeve. The sliders are located within the sliding slots. The upper end of the outer sleeve abuts against the first stop step. The upper end of the inner core passes through the cavity of the lower cylinder and extends into a cavity of the upper cylinder.

According to the vertebral body distraction support nail of the present invention, the upper support nail cap includes an upper cylinder and a lower cylinder which are integrally formed. An inner cylinder diameter of the upper cylinder is greater than an inner cylinder diameter of the lower cylinder. An outer side wall of the upper end of the outer sleeve is provided with sliding slots arranged axially. A lower part of a cavity of the lower cylinder is provided with sliders. An upper part of the cavity of the lower cylinder is provided with a first stop step. The lower part of the cavity of the lower cylinder is fitted over the upper end of the outer sleeve. The sliders are located within the sliding slots. The upper end of the outer sleeve abuts against the first stop step.

The upper end of the inner core passes through the cavity of the lower cylinder and extends into a cavity of the upper cylinder.

According to the vertebral body distraction support nail of the present invention, a second stop step is formed on an outer cylinder wall of the outer sleeve, and a lower end of the lower cylinder abuts against the second stop step.

According to the vertebral body distraction support nail of the present invention, the upper end of the inner core is of a prismatic structure. The pressure cap is of a cylindrical structure. A cavity of the pressure cap has a prismatic shape mating with the upper end of the inner core. The pressure cap is fitted over the upper end of the inner core. Engagement blocks are fixed on an outer cylinder wall of the pressure cap. Engagement slots are axially arranged on an inner cylinder wall of the upper cylinder. The engagement blocks are located within the engagement slots. The engagement blocks slide along the engagement slots. When the pressure cap slides up along the axial direction of the upper support nail cap to release the engagement blocks from the engagement slots, the pressure cap is still fitted over the upper end of the inner core.

According to the vertebral body distraction support nail of the present invention, an outer side wall of the upper end of the inner core is provided with protrusions arranged axially. Slots arranged axially are provided in a cavity of the pressure cap. The pressure cap is fitted over the upper end of the inner core. The protrusions are located within the slots. The protrusions slide along the slots. Engagement blocks are fixed on an outer cylinder wall of the pressure cap. Engagement slots are axially arranged on an inner cylinder wall of the upper cylinder. The engagement blocks are located within the engagement slots. The engagement blocks slide along the engagement slots. When the pressure cap slides up along the axial direction of the upper support nail cap to release the engagement blocks from the engagement slots, the pressure cap is still fitted over the upper end of the inner core, and the protrusions are located within the slots.

According to the vertebral body distraction support nail of the present invention, an outer side wall of the upper end of the inner core is provided with slots arranged axially. Protrusions arranged axially are provided in a cavity of the pressure cap. The pressure cap is fitted over the upper end of the inner core. The protrusions are located within the slots. The protrusions slide along the slots. Engagement blocks are fixed on an outer cylinder wall of the pressure cap. Engagement slots are axially arranged on an inner cylinder wall of the upper cylinder. The engagement blocks are located within the engagement slots. The engagement blocks slide along the engagement slots. When the pressure cap slides up along the axial direction of the upper support nail cap to release the engagement blocks from the engagement slots, the pressure cap is still fitted over the upper end of the inner core, and the protrusions are located within the slots.

When the vertebral body distraction support nail of the present invention is used, the tapered stapling head is aligned with a fractured vertebral body, and then the upper support nail cap is rotated to screw a lower end of the support nail body into the fractured vertebral body. In this process, the support nail body and the support nail cap rotate as a whole, that is, no relative rotation is generated between the support nail body and the support nail cap, between parts of the support nail body, and between parts of the support nail cap. Then, the pressure cap slides up along the axial direction of the upper support nail cap, such that the engagement and slidable connection between the pressure cap and the upper support nail cap is released. At this time, the pressure cap still keeps the engagement and slidable connection with the inner core. Then the upper support nail cap and the outer sleeve are kept still, and the pressure cap is rotated. The pressure cap drives the inner core to rotate. Because the inner core is threadedly connected to the outer sleeve, the inner core moves up relative to the outer sleeve, thus causing the tapered stapling head to move up and close to the lower end of the outer sleeve, such that the distraction ball performs distraction. The distraction ball in a distracted state supports the collapsed bony block of the fractured vertebral body, and it is only required to cut off the outer sleeve and the inner core at the outer side of the fractured vertebral body. Hence, in the present invention, the collapsed bony block may be distracted from the inside of the fractured vertebral body, so that the fractured vertebral body is reduced well, and occurrence of long-term complications is reduced.

The present invention will be further described below with reference to the accompanying drawings.

DESCRIPTION OF THE EMBODIMENTS

To make the foregoing objectives, features and advantages of the present invention more apparent and easier to be understood, specific embodiments of the present invention are illustrated in detail hereinafter in conjunction with the drawings.

The orientations or positional relationships indicated by the terms "upper", "lower", "front", "rear", "left" and "right" appearing in the embodiments of the present invention are based on the orientations or positional relationships shown in the accompanying drawings, are merely intended to facilitate describing the present invention and simplifying the description, rather than indicating or implying that the indicated apparatus must have a specific orientation, and be constructed and operated in a specific orientation, and therefore cannot be understood as a limitation to the present invention.

With respect to the description of the present invention, it should be noted that unless otherwise clearly specified or defined, the terms "provided", "mounted", "connected" and "coupled" should be understood in a broad sense, for example, may be a fixed connection, a detachable connection, or an integral connection; may be a mechanical connection; and may be a direct connection or an indirect connection through an intermediate medium. For persons skilled in the art, the specific meanings of the foregoing terms in the present invention can be understood according to the specific situations.

If the embodiments of the present invention relate to descriptions of "first", "second" and the like, the descriptions of "first", "second" and the like are used for descriptive purposes only and cannot be understood as indicating or implying their relative importance or implicitly indicating the number of indicated technical features.

Figure 1:
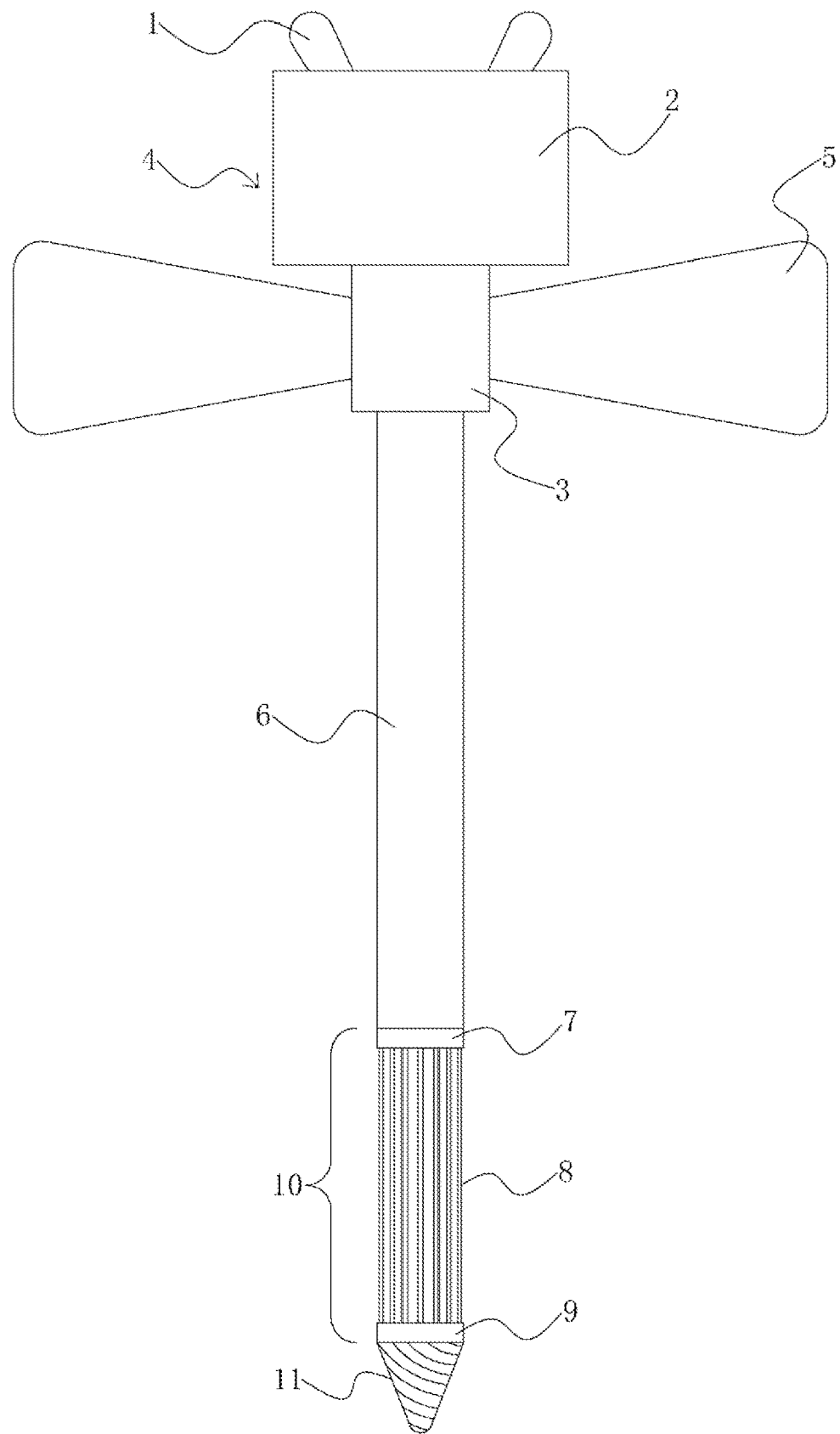
FIG. 1 is a front view of a vertebral body distraction support nail according to the present invention.
Figure 2:
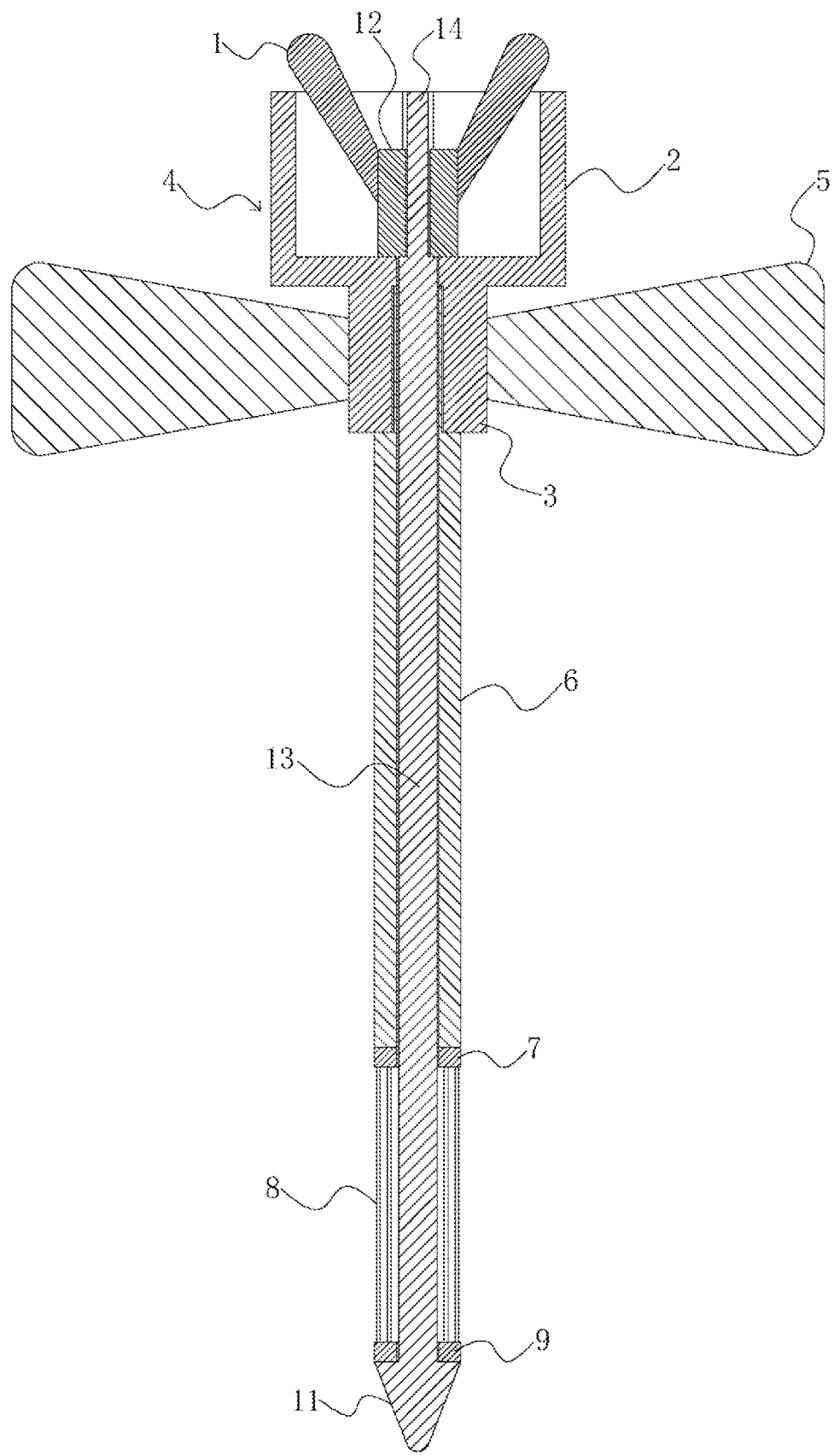
FIG. 2 is a front sectional view of a vertebral body distraction support nail according to the present invention.

As shown in FIG. 1, and in combination with FIG. 2 to FIG. 32, a vertebral body distraction support nail of the present invention includes a support nail body and a support nail cap. The support nail body includes an inner core 13, an outer sleeve 6 and a distraction ball 10. The inner core 13 is threadedly connected inside the outer sleeve 6. An upper end 14 and a lower end of the inner core 13 both extend to the outside of the outer sleeve 6. The lower end of the inner core 13 is provided with a tapered stapling head 11. The distraction ball 10 is fitted over the inner core 13 between the tapered stapling head 11 and the outer sleeve 6. The support nail cap includes an upper support nail cap 4 and a pressure cap 12. The upper support nail cap 4 is of a cylindrical structure. A lower end of a cavity of the upper support nail cap 4 is connected to an upper end 16 of the outer sleeve 6. The upper end 14 of the inner core 13 extends to an upper end of the cavity of the upper support nail cap 4. The pressure cap 12 is engaged with and slidably connected to the upper end 14 of the inner core 13. The pressure cap 12 is engaged with and slidably connected to the upper support nail cap 4. The pressure cap 12 slides along the inner core 13 and the upper support nail cap 4 in an axial direction. When the pressure cap 12 slides up along the axial direction of the upper support nail cap 4 and releases the engagement and slidable connection with the upper support nail cap 4, the pressure cap 12 still keeps the engagement and slidable connection with the inner core 13. When the tapered stapling head 11 moves close to the lower end of the outer sleeve 6, the distraction ball 10 performs distraction.

As shown in FIG. 29, FIG. 30, FIG. 31, and FIG. 32, when the present invention is used, the tapered stapling head 11 is aligned with a fractured vertebral body 22, and then the upper support nail cap 4 is rotated to screw a lower end of the support nail body into the fractured vertebral body 22. In this process, the support nail body and the support nail cap rotate as a whole, that is, no relative rotation is generated between the support nail body and the support nail cap, between parts of the support nail body, and between parts of the support nail cap. Then, the pressure cap 12 slides up along the axial direction of the upper support nail cap 4, such that the engagement and slidable connection between the pressure cap 12 and the upper support nail cap 4 is released. At this time, the pressure cap 12 still keeps the engagement and slidable connection with the inner core 13. Then the upper support nail cap 4 and the outer sleeve 6 are kept still, and the pressure cap 12 is rotated. The pressure cap 12 drives the inner core 13 to rotate. Because the inner core 13 is threadedly connected to the outer sleeve 6, the inner core 13 moves up relative to the outer sleeve 6, thus causing the tapered stapling head 11 to move up and close to the lower end of the outer sleeve 6, such that the distraction ball 10 performs distraction. The distraction ball 10 in a distracted state supports the collapsed bony block of the fractured vertebral body 22, and it is only required to cut off the outer sleeve 6 and the inner core 13 at the outer side of the fractured vertebral body 22. Hence, in the present invention, the collapsed bony block may be distracted from the inside of the fractured vertebral body 22, so that the fractured vertebral body 22 is reduced well, and occurrence of long-term complications is reduced.

As shown in FIG. 8 to FIG. 11, in combination with FIG. 29 to FIG. 32, the distraction ball 10 includes an upper sleeve ring 7 and a lower sleeve ring 9. The upper sleeve ring 7 and the lower sleeve ring 9 are both fitted over the inner core 13 between the tapered stapling head 11 and the lower end of the outer sleeve 6. The upper sleeve ring 7 abuts against the lower end of the outer sleeve 6. The lower sleeve ring 9 abuts against an upper end of the tapered stapling head 11. A plurality of distraction pieces 8 are fixedly connected between the upper sleeve ring 7 and the lower sleeve ring 9. The plurality of distraction pieces 8 are arranged around the circumference of the inner core 13. When the tapered stapling head 11 moves close to the lower end of the outer sleeve 6, the distraction pieces 8 bulge and deform away from the inner core 13, i.e., performing distraction.

As shown in FIG. 1, FIG. 2, and FIG. 29 to FIG. 32, in combination with FIG. 12 to FIG. 20, two first lugs 5 are fixedly connected on the upper support nail cap 4, and two second lugs 1 are fixedly connected on the pressure cap 12. The two first lugs 5 are fixedly connected to two opposite sides of the upper support nail cap 4, respectively, and the two second lugs 1 are fixedly connected to two opposite sides of the pressure cap 12, respectively. By configuring the lugs, the upper support nail cap 4 and the pressure cap 12 can be conveniently rotated.

As shown in FIG. 2 and FIG. 29 to FIG. 32, and in combination with FIG. 12 to FIG. 15, the upper support nail cap 4 includes an upper cylinder 2 and a lower cylinder 3 which are integrally formed. An inner cylinder diameter of the upper cylinder 2 is greater than an inner cylinder diameter of the lower cylinder 3, and an outer cylinder diameter of the upper cylinder 2 is also greater than an outer cylinder diameter of the lower cylinder 3. The two first lugs 5 are fixedly connected to two opposite sides of the lower cylinder 3, respectively. In combination with FIG. 5, FIG. 6, and FIG. 7, the upper end 16 of the outer sleeve 6 is of a hollow prismatic structure. A lower part of a cavity of the lower cylinder 3 is a prism mating with the upper end 16 of the outer sleeve 6. An upper part of the cavity of the lower cylinder 3 is provided with a first stop step 20. The lower part of the cavity of the lower cylinder 3 is fitted over the upper end 16 of the outer sleeve 6. The upper end 16 of the outer sleeve 6 abuts against the first stop step 20. The upper end 14 of the inner core 13 passes through the cavity of the lower cylinder 3 and extends into a cavity of the upper cylinder 2.

In the present embodiment, the upper end 16 of the outer sleeve 6 is of a hollow triangular prism structure, and the lower part of the cavity of the lower cylinder 3 is also a triangular prism mating with the upper end 16 of the outer sleeve 6. The first stop step 20 is formed in the following mode: the upper part of the cavity of the lower cavity 3 is cylindrical, and a pore diameter of the cylindrical cavity is less than a pore diameter of the triangular prism cavity below. Thus, the first stop step 20 is formed between the upper part and the lower part of the cavity of the lower cylinder 3, that is, the first stop step 20 is formed on the upper part of the cavity of the lower cylinder 3.

Figure 25:
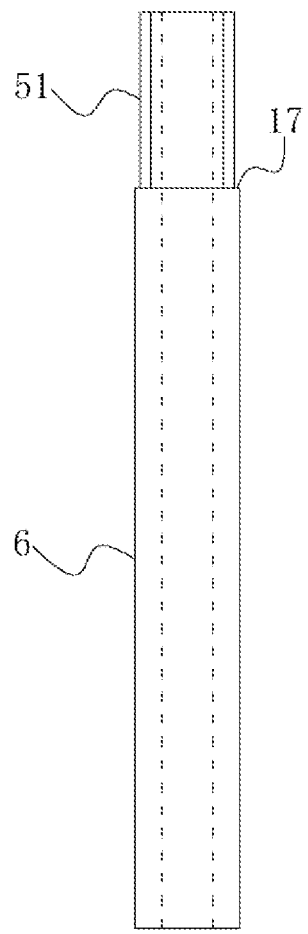
FIG. 25 is another front view of an outer sleeve according to the present invention.
Figure 26:
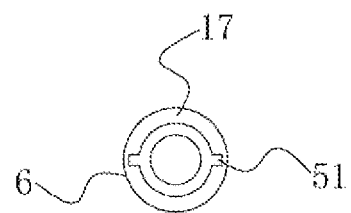
FIG. 26 is a top view of FIG. 25.
Figure 27:
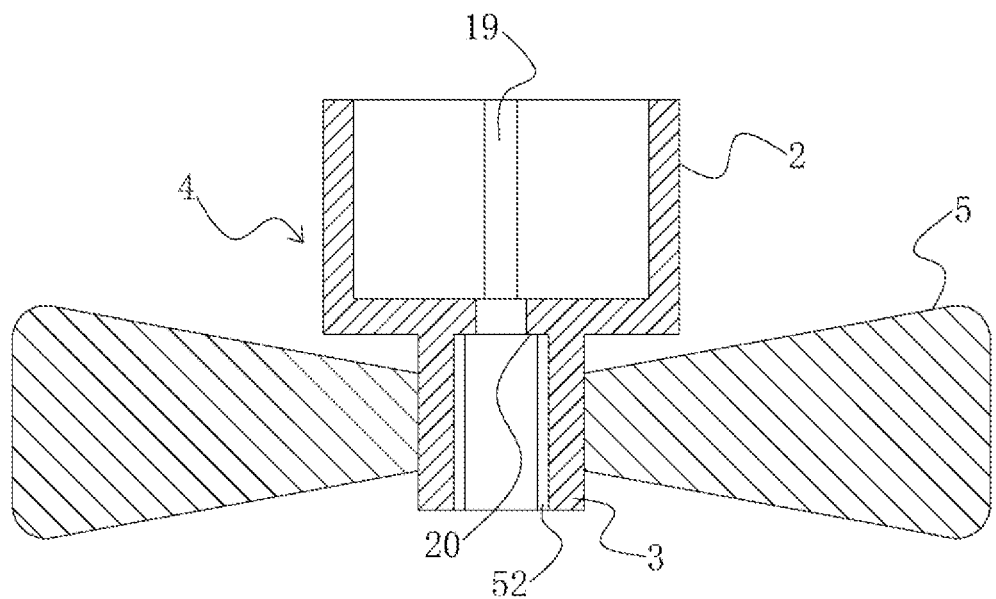
FIG. 27 is another front sectional view of an upper support nail cap according to the present invention.
Figure 28:
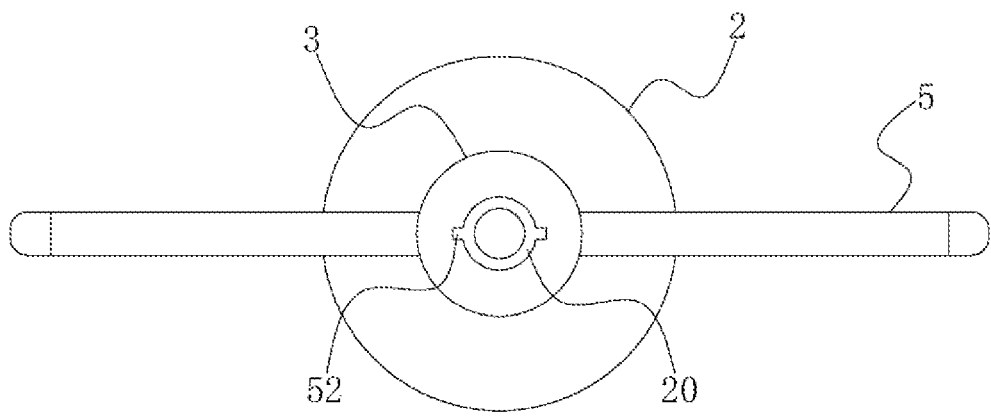
FIG. 28 is another bottom view of an upper support nail cap according to the present invention.
Figure 29:
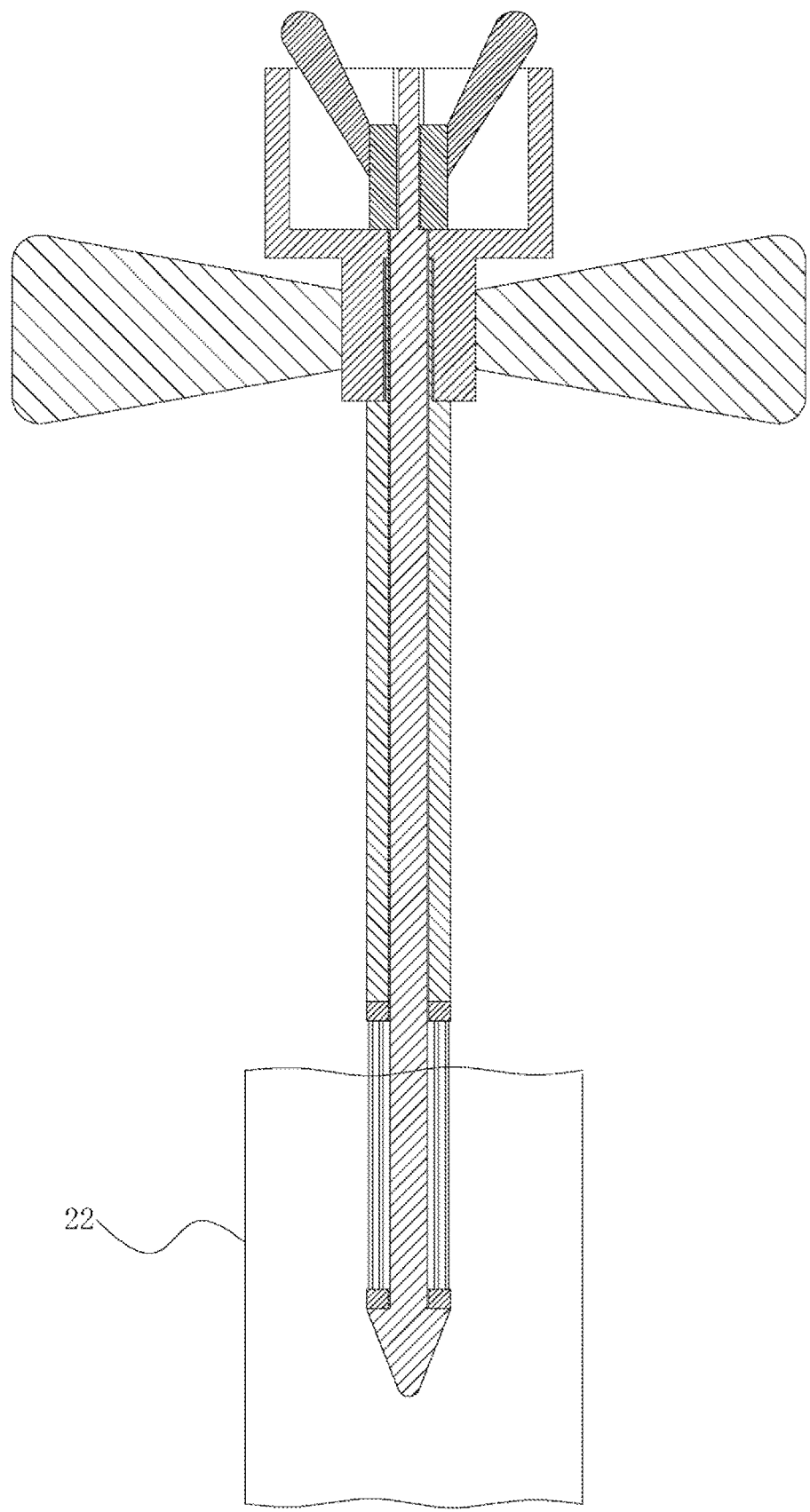
FIG. 29 is a view showing a first use state of a vertebral body distraction support nail according to the present invention.

Except the connection mode of the lower cylinder 3 and the outer sleeve 6 above, the lower cylinder 3 and the outer sleeve 6 can also be connected in the following mode: as shown in FIG. 25, and in combination with FIG. 26 to FIG. 28, an outer side wall of the upper end 16 of the outer sleeve 6 is provided with sliders 51. A lower part of a cavity of the lower cylinder 3 is provided with sliding slots 52 arranged axially. After the lower part of the cavity of the lower cylinder 3 is fitted over the upper end 16 of the outer sleeve 6, the sliders 51 are located within the sliding slots 52. Certainly, the positions of the sliders 51 and the sliding slots 52 can be exchanged. That is, the outer side wall of the upper end 16 of the outer sleeve 6 is provided with the sliding slots 52 arranged axially, and the lower part of the cavity of the lower cylinder 3 is provided with sliders 51. After the lower part of the cavity of the lower cylinder 3 is fitted over the upper end 16 of the outer sleeve 6, the sliders 51 are located within the sliding slots 52.

After the lower part of the cavity of the lower cylinder 3 is fitted over the upper end 16 of the outer sleeve 6, interference fit, or clearance fit, is achieved between the lower cylinder 3 and the upper end 16 of the outer sleeve 6 because both of the fitting modes can ensure that the upper support nail cap 4 and the outer sleeve 6 are rotated or not rotated together. That is, when the upper support nail cap 4 is rotated, the upper support nail cap 4 drives the outer sleeve 6 to rotate synchronously, and when the upper support nail cap 4 does not rotate, the outer sleeve 6 likewise does not rotate.

Figure 5:
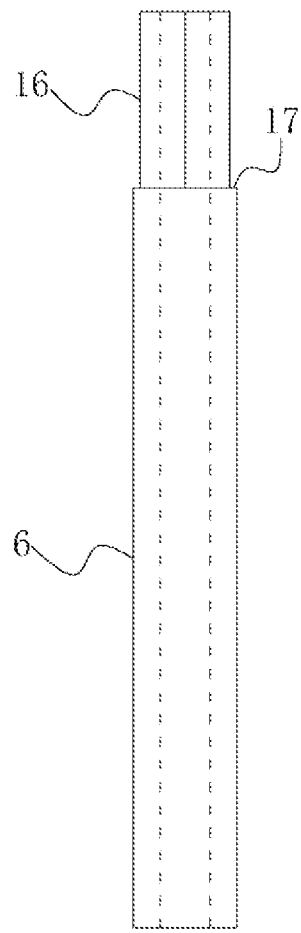
FIG. 5 is a front view of an outer sleeve according to the present invention.
Figure 6:
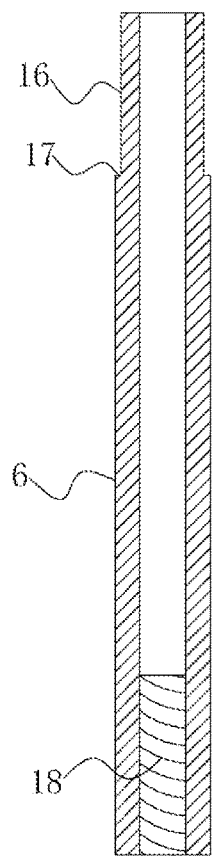
FIG. 6 is a front sectional view of an outer sleeve according to the present invention.
Figure 7:
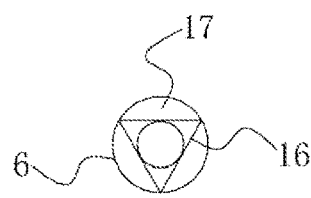
FIG. 7 is a top view of FIG. 5.
Figure 8:
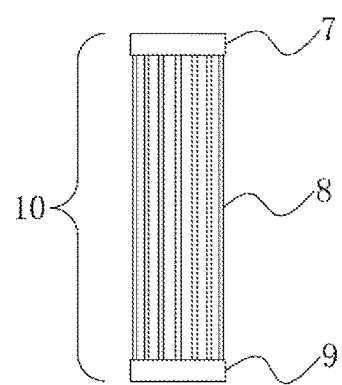
FIG. 8 is a front view of a distraction ball (the distraction ball being in a contracted state) according to the present invention.
Figure 9:
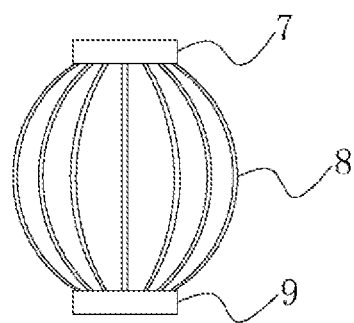
FIG. 9 is a front view of a distraction ball (the distraction ball being in a distracted state) according to the present invention.
Figure 10:
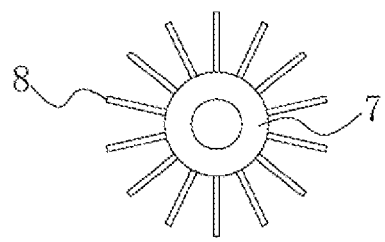
FIG. 10 is a top view of FIG. 9.
Figure 11:
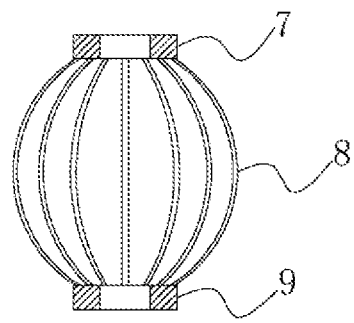
FIG. 11 is a front sectional view of a distraction ball (the distraction ball being in a distracted state) according to the present invention.
Figure 12:
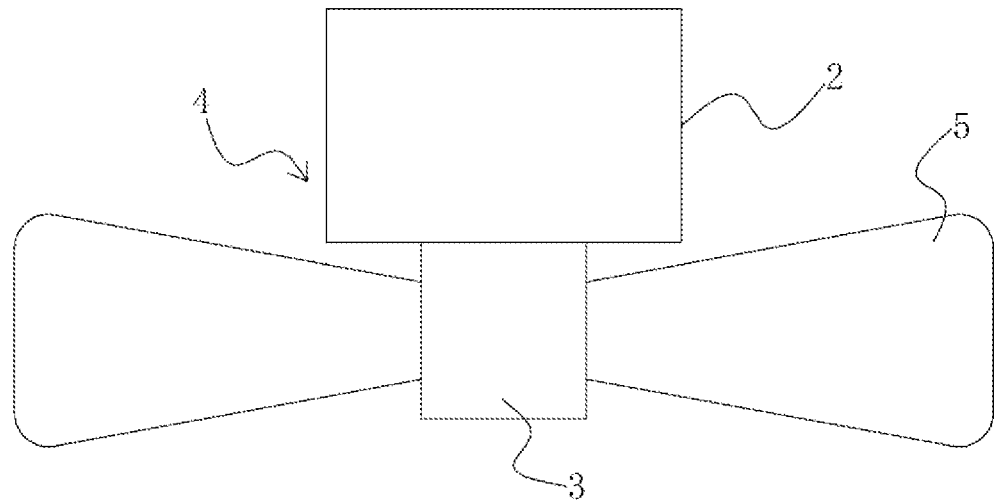
FIG. 12 is a front view of an upper support nail cap according to the present invention.
Figure 13:
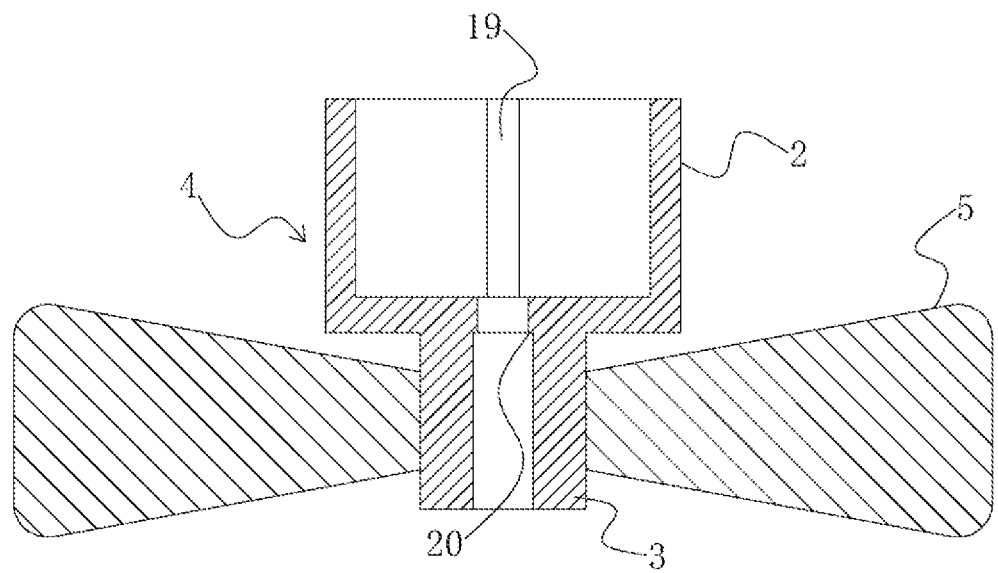
FIG. 13 is a front sectional view of an upper support nail cap according to the present invention.
Figure 14:
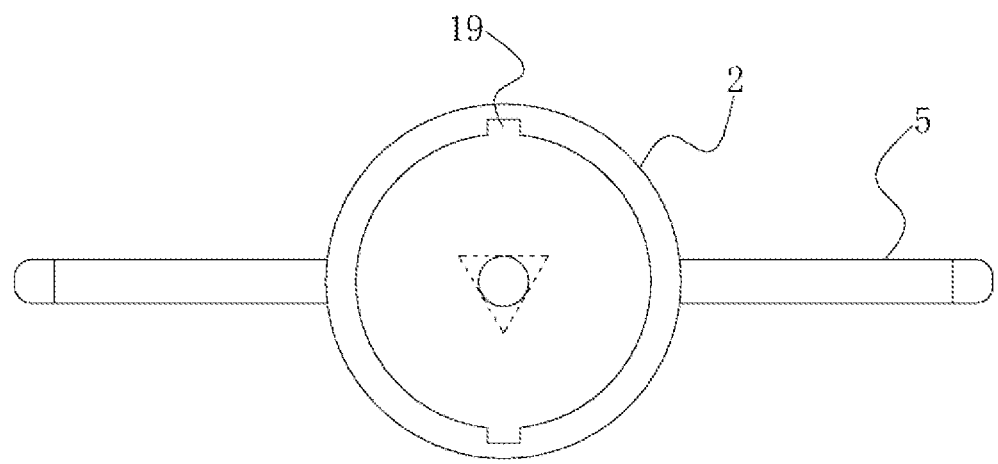
FIG. 14 is a top view of an upper support nail cap according to the present invention.
Figure 15:
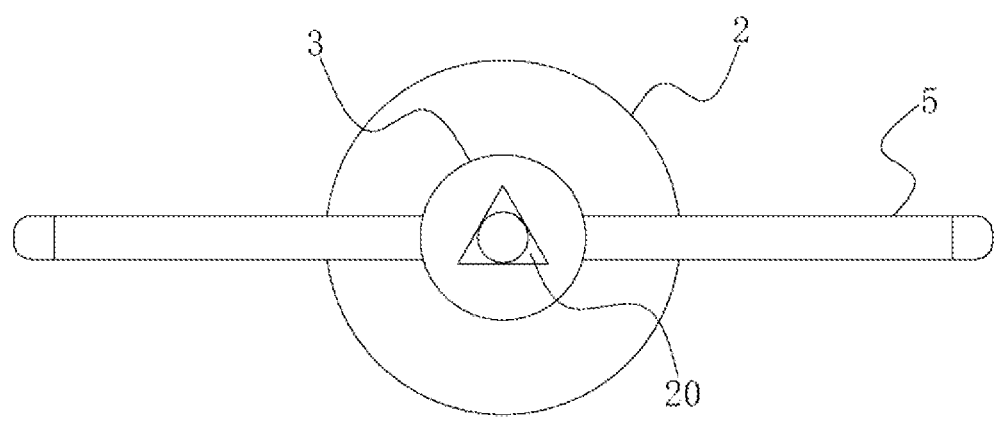
FIG. 15 is a bottom view of an upper support nail cap according to the present invention.
Figure 16:
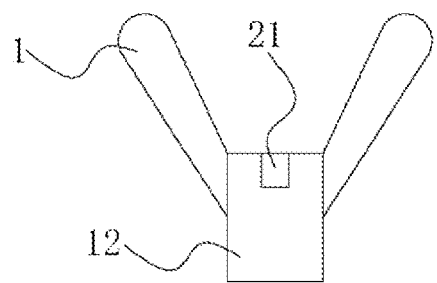
FIG. 16 is a front view of a pressure cap according to the present invention.
Figure 17:
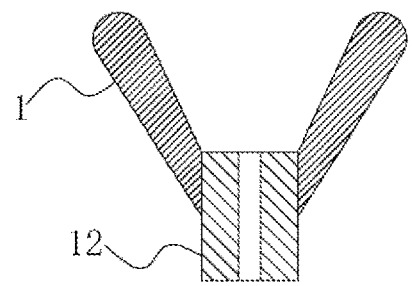
FIG. 17 is a front sectional view of a pressure cap according to the present invention.
Figure 18:
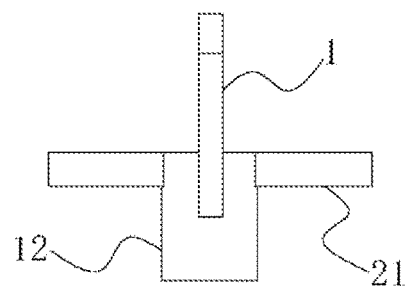
FIG. 18 is a left view (also a right view) of a pressure cap according to the present invention.
Figure 19:
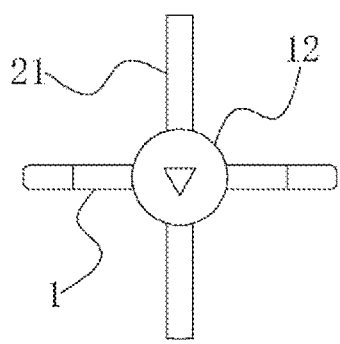
FIG. 19 is a top view of a pressure cap according to the present invention.
Figure 20:
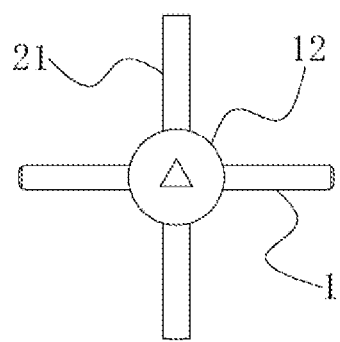
FIG. 20 is a bottom view of a pressure cap according to the present invention.

As shown in FIG. 2 and FIG. 29 to FIG. 32, and in combination with FIG. 5, FIG. 6, and FIG. 7, a second stop step 17 is formed on an outer cylinder wall of the outer sleeve 6, and a lower end of the lower cylinder 3 abuts against the second stop step 17, such that the lower cylinder 3 more closely fits the outer sleeve 6. The second stop step 17 is formed in the following mode: no matter how the upper end 16 of the outer sleeve 6 is connected to the lower cylinder 3, as long as the upper end 16 of the outer sleeve 6 has a part an outer diameter of which is less than an outer diameter of the lower end, the second stop step 17 is formed between the upper end and the lower end. Taking FIG. 5, FIG. 6, and FIG. 7 as an example, the outer diameter at three sides of the hollow triangular prism structure of the upper end of the outer sleeve 6 is less than the outer diameter of the lower end of the outer sleeve 6, such that the second stop step 17 is formed between the upper end and the lower end of the outer sleeve 6.

As shown in FIG. 2 and FIG. 29 to FIG. 32, and in combination with FIG. 3, FIG. 4, FIG. 13, FIG. 14, and FIG. 16 to FIG. 20, the upper end 14 of the inner core 13 is of a prismatic structure. The pressure cap 12 is of a cylindrical structure. A cavity of the pressure cap 12 has a prismatic shape mating with the upper end 14 of the inner core 13. The pressure cap 12 is fitted over the upper end 14 of the inner core 13. Engagement blocks 21 are fixed on an outer cylinder wall of the pressure cap 12. Engagement slots 19 are axially arranged on an inner cylinder wall of the upper cylinder 2. The engagement blocks 21 are located within the engagement slots 19. The engagement blocks 21 slide along the engagement slots 19. When the pressure cap 12 slides up along the axial direction of the upper support nail cap 4 to release the engagement blocks 21 from the engagement slots 19, the pressure cap 12 is still fitted over the upper end 14 of the inner core 13.

In the present embodiment, the upper end 14 of the inner core 13 is of a hollow triangular prism structure, and the cavity of the pressure cap 12 is a triangular prism mating with the upper end 14 of the inner core 13. Thus, after the pressure cap 12 is fitted over the upper end 14 of the inner core 13, engagement and slidable connection are achieved between the pressure cap 12 and the inner core 13. That is, the pressure cap 12 slides up and down along the axial direction of the inner core 13. However, the pressure cap 12 cannot circumferentially rotate relative to the inner core 13, and can only drive the inner core 13 to rotate synchronously when the pressure cap 12 is rotated. When the pressure cap 12 does not rotate, the inner core 13 likewise does not rotate.

Figure 30:
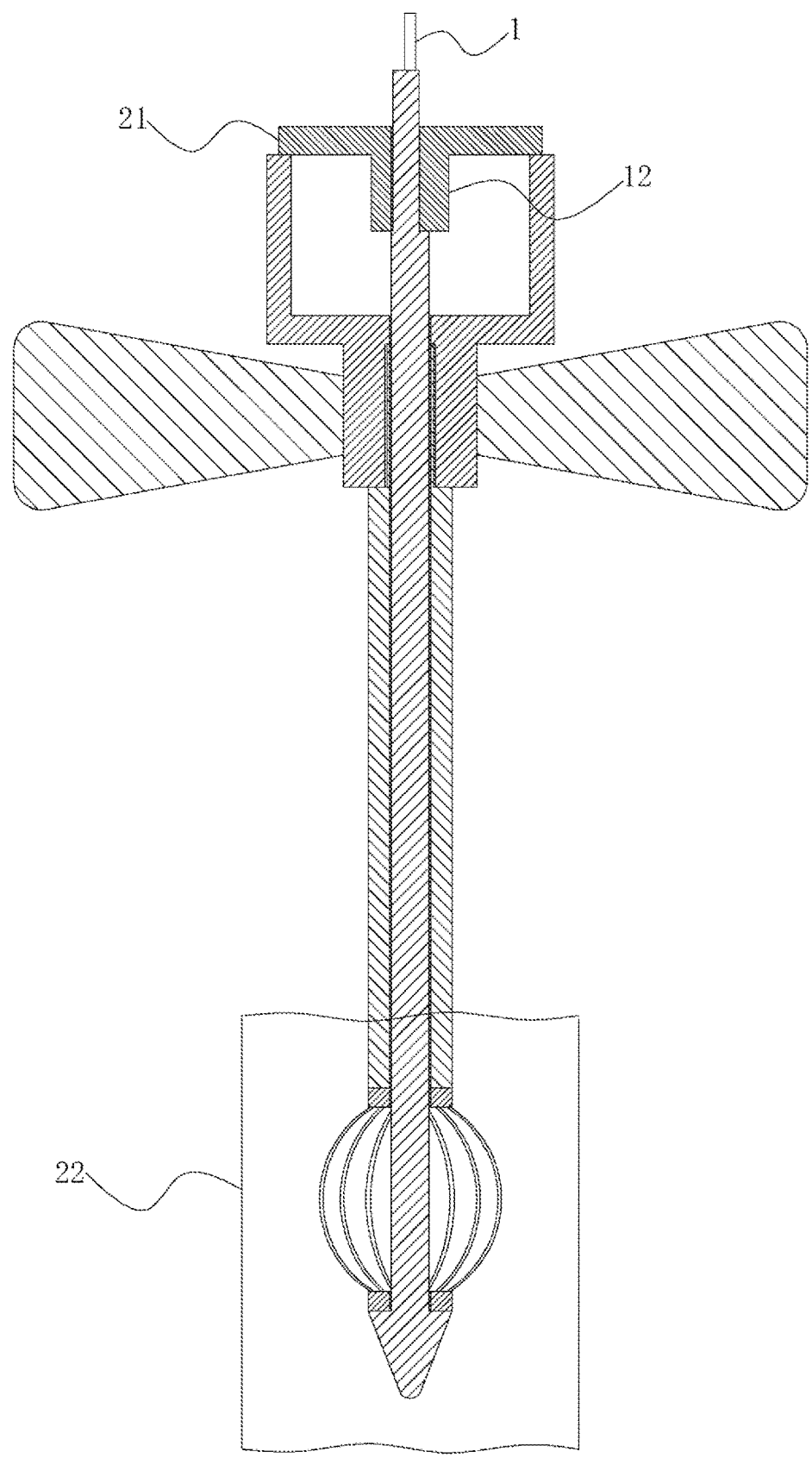
FIG. 30 is a view showing a second use state of a vertebral body distraction support nail according to the present invention.
Figure 31:
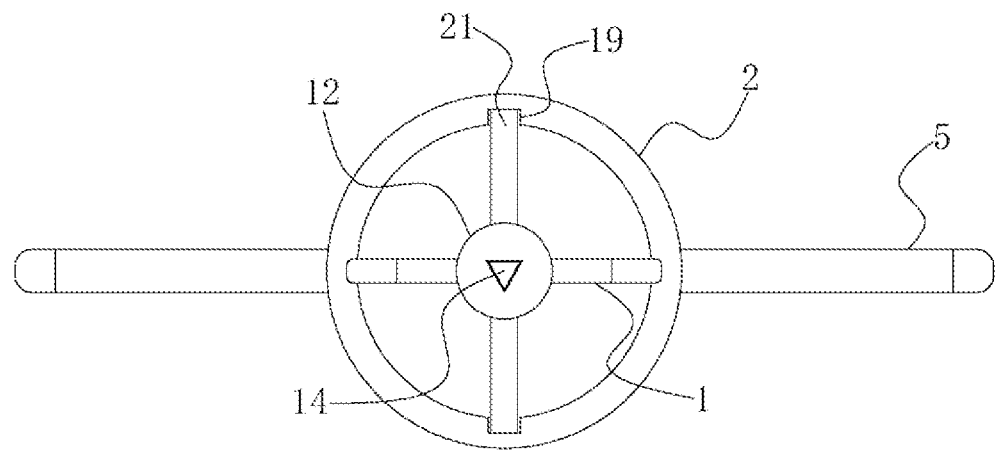
FIG. 31 is a top view of the vertebral body distraction support nail according to the present invention shown in FIG. 29.
Figure 32:
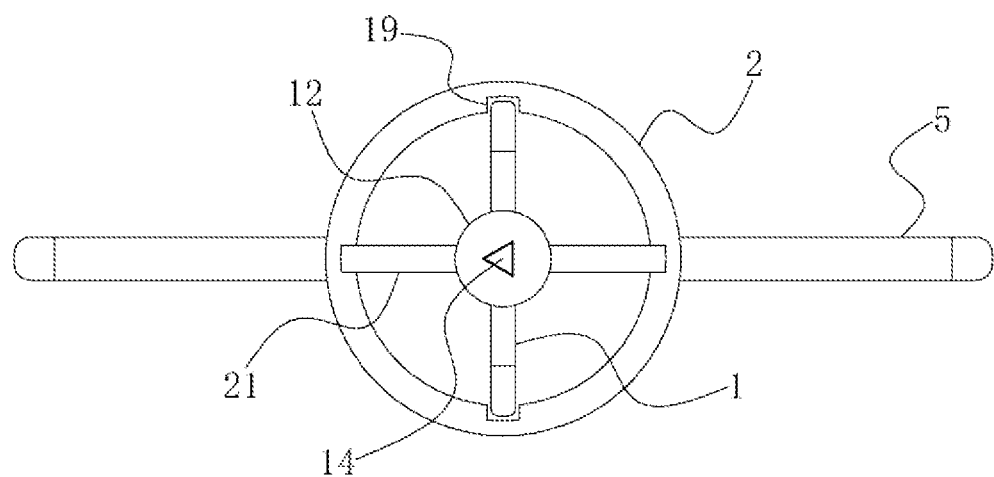
FIG. 32 is a top view of the vertebral body distraction support nail according to the present invention shown in FIG. 30.

The pressure cap 12 is engaged with and rotatably connected to the upper support nail cap 4 by means of the engagement blocks 21 and the engagement slots 19. That is, the pressure cap 12 slides up and down along the axial direction of the upper support nail cap 4. At this time, the engagement blocks 21 slide up and down along the engagement slots 19. However, because of a limiting function of the engagement blocks 21 and the engagement slots 19, the pressure cap 12 cannot circumferentially rotate relative to the upper support nail cap 4, and the pressure cap 12 and the upper support nail cap 4 can only rotate synchronously. That is, when the upper support nail cap 4 is rotated, the pressure cap 12 is driven to rotate synchronously. When the pressure cap 12 slides up along the axial direction of the upper support nail cap 4 to release the engagement blocks 21 from the engagement slots 19, the engagement and slidable connection between the pressure cap 12 and the upper support nail cap 4 is released. Moreover, at this time, the pressure cap 12 is still fitted over the upper end 14 of the inner core 13. That is, the pressure cap 12 is still engaged with and slidably connected to the upper end 14 of the inner core 13. At this time, when the pressure cap 12 is rotated, the pressure cap 12 drives the inner core 13 to rotate together relative to the upper support nail cap 4. In order to facilitate operation, when the pressure cap 12 is rotated, the engagement blocks 21 slide against the upper end face of the upper cylinder 2 (as shown in FIG. 30). Because the upper support nail cap 4 and the outer sleeve 6 are kept rotating synchronously or not rotating, and the inner core 13 is threadedly connected to the outer sleeve 6, when the pressure cap 12 drives the inner core 13 to rotate relative to the upper support nail cap 4, the inner core 13 also rotates relative to the outer sleeve 6, and thus, the inner core 13 moves up relative to the outer sleeve 6. Therefore, the tapered stapling head 11 at the lower end of the inner core 13 moves close to the lower end of the outer sleeve 6, and thus presses the upper sleeve ring 7 and the lower sleeve ring 9 of the distraction ball 10, such that the two sleeve rings move close to each other, and the distraction pieces 8 bulge and deform away from the inner core 13, i.e., being in a distracted state, as shown in FIG. 30.

Figure 3:
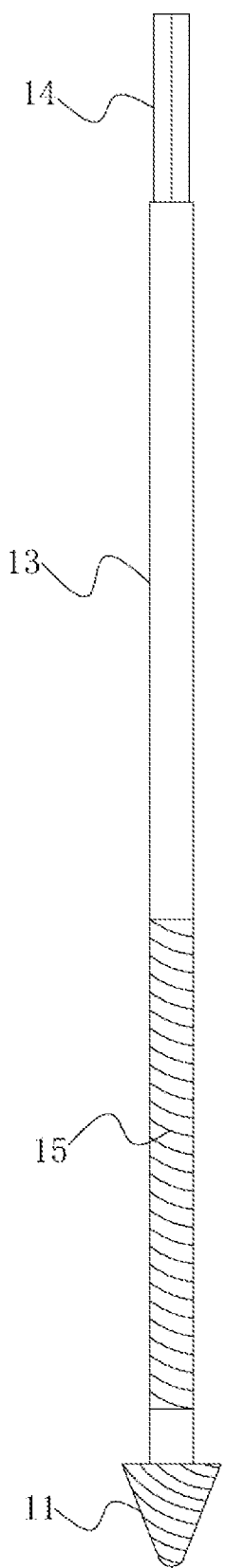
FIG. 3 is a front view of an inner core according to the present invention.
Figure 4:
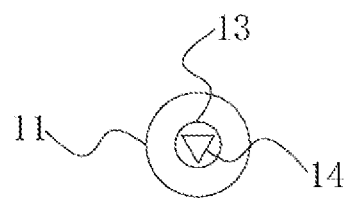
FIG. 4 is a top view of FIG. 3.

As shown in FIG. 3 and FIG. 6, screw-in threads are formed on an outer side wall of the tapered stapling head 11, such that the tapered stapling head 11 can easily be screwed in the fractured vertebral body 22. Outer threads 15 are further provided on an outer side wall of a core body between the two ends of the inner core 13. Inner threads 18 are formed on an inner cylinder wall of the outer sleeve 6. The inner core 13 is threadedly connected to the outer sleeve 6 by means of the outer threads 15 and the inner threads 18. When the inner core 13 is rotated relative to the outer sleeve 6, the inner core 13 moves up or down relative to the outer sleeve 6. In the present embodiment, in order to make the tapered stapling head 11 move close to the lower end of the outer sleeve 6 and make the distraction ball 10 be in the distracted state, the inner core 13 can only move up relative to the outer sleeve 6.

Figure 21:
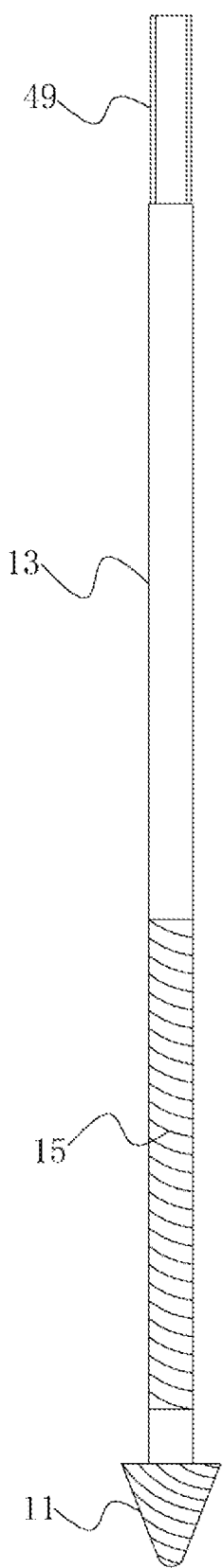
FIG. 21 is another front view of an inner core according to the present invention.
Figure 22:
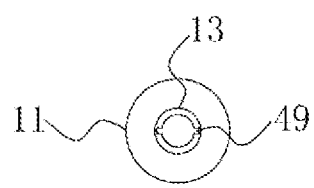
FIG. 22 is a top view of FIG. 21.
Figure 23:
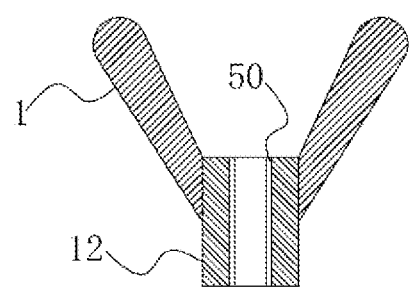
FIG. 23 is another front sectional view of a pressure cap according to the present invention.
Figure 24:
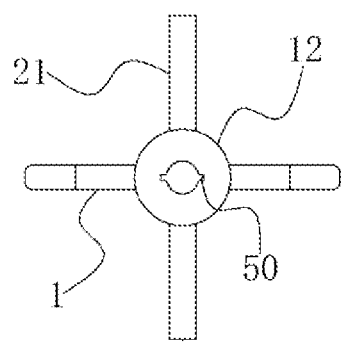
FIG. 24 is another top view of a pressure cap according to the present invention.

Certainly, the pressure cap 12 may also be engaged with and slidably connected to the upper end of the inner core 13 by using the following mode: as shown in FIG. 21, and in combination with FIG. 22 to FIG. 24, the outer side wall of the upper end 14 of the inner core 13 is provided with protrusions 49 arranged axially. Slots 50 arranged axially are provided in the cavity of the pressure cap 12. When the pressure cap 12 is fitted over the upper end 14 of the inner core 13, the protrusions 49 are located within the slots 50. The protrusions 49 may slide along the slots 50. When the pressure cap 12 slides up along the axial direction of the upper support nail cap 4 to release the engagement blocks 21 from the engagement slots 19, the pressure cap 12 is still fitted over the upper end 14 of the inner core 13, and the protrusions 49 are located within the slots 50. Certainly, the positions of the protrusions 49 and the slots 50 can be exchanged. That is, the outer side wall of the upper end 14 of the inner core 13 is provided with slots 50 arranged axially, and protrusions 49 arranged axially are provided in the cavity of the pressure cap 12. Due to a limiting function of the protrusions 49 and the slots 50, the pressure cap 12 slides up and down along the axial direction of the inner core 13. In this process, the protrusions 49 also slide up and down along the slots 50. However, the pressure cap 12 cannot circumferentially rotate relative to the inner core 13, and can only drive the inner core 13 to rotate synchronously when the pressure cap 12 is rotated. When the pressure cap 12 does not rotate, the inner core 13 likewise does not rotate.

As shown in FIG. 29 to FIG. 32, when the present invention is used, the tapered stapling head 11 is aligned with a fractured vertebral body 22, and then the upper support nail cap 4 is rotated by the first lugs 5 to screw a lower end of the support nail body into the fractured vertebral body 22. In this process, the support nail body and the support nail cap rotate as a whole, that is, no relative rotation is generated between the support nail body and the support nail cap, between parts of the support nail body, and between parts of the support nail cap. Then, the pressure cap 12 slides up along the axial direction of the upper support nail cap 4, such that the engagement and slidable connection between the pressure cap 12 and the upper support nail cap 4 is released (i.e., the engagement blocks 21 are released from the engagement slots 19). At this time, the pressure cap 12 still keeps the engagement and slidable connection with the inner core 13. Then the upper support nail cap 4 and the outer sleeve 6 are kept still, and the pressure cap 12 is rotated by the second lugs 1. The pressure cap 12 drives the inner core 13 to rotate. Because the inner core 13 is threadedly connected to the outer sleeve 6, the inner core 13 moves up relative to the outer sleeve 6, thus causing the tapered stapling head 11 to move up and closet to the lower end of the outer sleeve 6, such that the distraction ball 10 performs distraction. The distraction ball 10 in a distracted state supports the collapsed bony block of the fractured vertebral body 22, and it is only required to cut off the outer sleeve 6 and the inner core 13 at the outer side of the fractured vertebral body 22. After the reduction operation is completed, the distraction ball 10 and parts of the inner core 13 and the outer sleeve 6 are left in the fractured vertebral body 22, and are no longer removed. Because the inner core 13 and the outer sleeve 6 which are left in the fractured vertebral body 22 are still threadedly connected, the distraction ball 10 in the fractured vertebral body 22 is kept in the distracted state. Hence, in the present invention, the collapsed bony block may be distracted from the inside of the fractured vertebral body 22, so that the fractured vertebral body 22 is reduced well, and occurrence of long-term complications is reduced.

According to the present invention, compressed vertebral body can be distracted after support nail placement in injured vertebra, so that the vertebral body is better reduced. An anterior vertebral body is supported, which greatly avoids the occurrence of an internal fixation failure in the long term. Moreover, the materials of the distraction piece 10, the inner core 13 and the outer sleeve 6 are all titanium alloy or tantalum metal, which have better compatibility with bones, achieving better bone healing and bone ingrowth.

The foregoing embodiments are only for describing the preferred embodiments of the present invention, and are not intended to limit the scope of the present invention. Various modifications and improvements made by persons skilled in the art to the technical solutions of the present invention shall fall within the scopes of protection determined by the claims of the present invention without departing from the design spirit of the present invention.

INDUSTRIAL APPLICABILITY

A vertebral body distraction support nail according to embodiments of the present invention includes a support nail body and a support nail cap. The support nail body includes an inner core, an outer sleeve and a distraction ball. The inner core is threadedly connected inside the outer sleeve. An upper end and a lower end of the inner core both extend to the outside of the outer sleeve. The lower end of the inner core is provided with a tapered stapling head. The distraction ball is fitted over the inner core between the tapered stapling head and the outer sleeve. The support nail cap includes an upper support nail cap and a pressure cap. The upper support nail cap is of a cylindrical structure. A lower end of a cavity of the upper support nail cap is connected to an upper end of the outer sleeve. The upper end of the inner core extends to an upper end of the cavity of the upper support nail cap. The pressure cap is engaged with and slidably connected to the upper end of the inner core. The pressure cap is engaged with and slidably connected to the upper support nail cap. In the present invention, a collapsed bony block may be distracted from the inside of a fractured vertebral body, so that the fractured vertebral body is reduced well, and occurrence of long-term complications is reduced. The present invention has good application and promotion value, and can be produced in batches.

The invention claimed is:

1. A vertebral body distraction tool, comprising a tool body and a tool cap, wherein the tool body comprises an inner core, an outer sleeve and a distraction ball; the inner core is threadedly connected inside the outer sleeve; an upper end and a lower end of the inner core both extend to the outside of the outer sleeve; the lower end of the inner core is provided with a tapered stapling head; the distraction ball is fitted over the inner core between the tapered stapling head and the outer sleeve; the tool cap comprises an upper tool cap and a pressure cap; the upper tool cap is of a cylindrical structure; a lower end of a cavity of the upper tool cap is connected to an upper end of the outer sleeve; the upper end of the inner core extends to an upper end of the cavity of the upper tool cap; the pressure cap is engaged with and slidably connected to the upper end of the inner core; the pressure cap is engaged with and slidably connected to the upper tool cap; the pressure cap slides along the inner core and the upper tool cap in an axial direction; when the pressure cap slides up along the axial direction of the upper tool cap to release the engagement and slidable connection with the upper tool cap, the pressure cap still keeps the engagement and slidable connection with the inner core; and when the tapered stapling head moves close to the lower end of the outer sleeve, the distraction ball performs distraction.

2. The vertebral body distraction tool according to claim 1, wherein the distraction ball comprises an upper sleeve ring and a lower sleeve ring; the upper sleeve ring and the lower sleeve ring are both fitted over the inner core between the tapered stapling head and the lower end of the outer sleeve; the upper sleeve ring abuts against the lower end of the outer sleeve; the lower sleeve ring abuts against an upper end of the tapered stapling head; a plurality of distraction pieces are fixedly connected between the upper sleeve ring and the lower sleeve ring; the plurality of distraction pieces are arranged around the circumference of the inner core; and when the tapered stapling head moves close to the lower end of the outer sleeve, the distraction pieces bulge and deform away from the inner core.

3. The vertebral body distraction tool according to claim 2, wherein two first lugs are fixedly connected on the upper tool cap, and two second lugs are fixedly connected on the pressure cap.

4. The vertebral body distraction tool according to claim 3, wherein the upper tool cap comprises an upper cylinder and a lower cylinder which are integrally formed; an inner cylinder diameter of the upper cylinder is greater than an inner cylinder diameter of the lower cylinder; the upper end of the outer sleeve is of a hollow prismatic structure; a lower part of a cavity of the lower cylinder is a prism mating with the upper end of the outer sleeve; an upper part of the cavity of the lower cylinder is provided with a first stop step; the lower part of the cavity of the lower cylinder is fitted over the upper end of the outer sleeve; the upper end of the outer sleeve abuts against the first stop step; and the upper end of the inner core passes through the cavity of the lower cylinder and extends into a cavity of the upper cylinder.

5. The vertebral body distraction tool according to claim 3, wherein the upper tool cap comprises an upper cylinder and a lower cylinder which are integrally formed; an inner cylinder diameter of the upper cylinder is greater than an inner cylinder diameter of the lower cylinder; an outer side wall of the upper end of the outer sleeve is provided with sliders; a lower part of a cavity of the lower cylinder is provided with sliding slots arranged axially; an upper part of the cavity of the lower cylinder is provided with a first stop step; the lower part of the cavity of the lower cylinder is fitted over the upper end of the outer sleeve; the sliders are located within the sliding slots; the upper end of the outer sleeve abuts against the first stop step; and the upper end of the inner core passes through the cavity of the lower cylinder and extends into a cavity of the upper cylinder.

6. The vertebral body distraction tool according to claim 3, wherein the upper tool cap comprises an upper cylinder and a lower cylinder which are integrally formed; an inner cylinder diameter of the upper cylinder is greater than an inner cylinder diameter of the lower cylinder; an outer side wall of the upper end of the outer sleeve is provided with sliding slots arranged axially; a lower part of a cavity of the lower cylinder is provided with sliders; an upper part of the cavity of the lower cylinder is provided with a first stop step; the lower part of the cavity of the lower cylinder is fitted over the upper end of the outer sleeve; the sliders are located within the sliding slots; the upper end of the outer sleeve abuts against the first stop step; and the upper end of the inner core passes through the cavity of the lower cylinder and extends into a cavity of the upper cylinder.

7. The vertebral body distraction tool according to claim 4, wherein a second stop step is formed on an outer cylinder wall of the outer sleeve, and a lower end of the lower cylinder abuts against the second stop step.

8. The vertebral body distraction tool according to claim 7, wherein the upper end of the inner core is of a prismatic structure; the pressure cap is of a cylindrical structure; a cavity of the pressure cap has a prismatic shape mating with the upper end of the inner core; the pressure cap is fitted over the upper end of the inner core; engagement blocks are fixed on an outer cylinder wall of the pressure cap; engagement slots are axially arranged on an inner cylinder wall of the upper cylinder; the engagement blocks are located within the engagement slots; the engagement blocks slide along the engagement slots; and when the pressure cap slides up along the axial direction of the upper tool cap to release the engagement blocks from the engagement slots, the pressure cap is still fitted over the upper end of the inner core.

9. The vertebral body distraction tool according to claim 7, wherein an outer side wall of the upper end of the inner core is provided with protrusions arranged axially; slots arranged axially are provided in a cavity of the pressure cap; the pressure cap is fitted over the upper end of the inner core; the protrusions are located within the slots; the protrusions slide along the slots; engagement blocks are fixed on an outer cylinder wall of the pressure cap; engagement slots are axially arranged on an inner cylinder wall of the upper cylinder; the engagement blocks are located within the engagement slots; the engagement blocks slide along the engagement slots; and when the pressure cap slides up along the axial direction of the upper tool cap to release the engagement blocks from the engagement slots, the pressure cap is still fitted over the upper end of the inner core, and the protrusions are located within the slots.

10. The vertebral body distraction tool according to claim 7, wherein an outer side wall of the upper end of the inner core is provided with slots arranged axially; protrusions arranged axially are provided in a cavity of the pressure cap; the pressure cap is fitted over the upper end of the inner core; the protrusions are located within the slots; the protrusions slide along the slots; engagement blocks are fixed on an outer cylinder wall of the pressure cap; engagement slots are axially arranged on an inner cylinder wall of the upper cylinder; the engagement blocks are located within the engagement slots; the engagement blocks slide along the engagement slots; and when the pressure cap slides up along the axial direction of the upper tool cap to release the engagement blocks from the engagement slots, the pressure cap is still fitted over the upper end of the inner core, and the protrusions are located within the slots.

11. The vertebral body distraction tool according to claim 5, wherein a second stop step is formed on an outer cylinder wall of the outer sleeve, and a lower end of the lower cylinder abuts against the second stop step.

12. The vertebral body distraction tool according to claim 11, wherein the upper end of the inner core is of a prismatic structure; the pressure cap is of a cylindrical structure; a cavity of the pressure cap has a prismatic shape mating with the upper end of the inner core; the pressure cap is fitted over the upper end of the inner core; engagement blocks are fixed on an outer cylinder wall of the pressure cap; engagement slots are axially arranged on an inner cylinder wall of the upper cylinder; the engagement blocks are located within the engagement slots; the engagement blocks slide along the engagement slots; and when the pressure cap slides up along the axial direction of the upper tool cap to release the engagement blocks from the engagement slots, the pressure cap is still fitted over the upper end of the inner core.

13. The vertebral body distraction tool according to claim 11, wherein an outer side wall of the upper end of the inner core is provided with protrusions arranged axially; slots arranged axially are provided in a cavity of the pressure cap; the pressure cap is fitted over the upper end of the inner core; the protrusions are located within the slots; the protrusions slide along the slots; engagement blocks are fixed on an outer cylinder wall of the pressure cap; engagement slots are axially arranged on an inner cylinder wall of the upper cylinder; the engagement blocks are located within the engagement slots; the engagement blocks slide along the engagement slots; and when the pressure cap slides up along the axial direction of the upper tool cap to release the engagement blocks from the engagement slots, the pressure cap is still fitted over the upper end of the inner core, and the protrusions are located within the slots.

14. The vertebral body distraction tool according to claim 11, wherein an outer side wall of the upper end of the inner core is provided with slots arranged axially; protrusions arranged axially are provided in a cavity of the pressure cap; the pressure cap is fitted over the upper end of the inner core; the protrusions are located within the slots; the protrusions slide along the slots; engagement blocks are fixed on an outer cylinder wall of the pressure cap; engagement slots are axially arranged on an inner cylinder wall of the upper cylinder; the engagement blocks are located within the engagement slots; the engagement blocks slide along the engagement slots; and when the pressure cap slides up along the axial direction of the upper tool cap to release the engagement blocks from the engagement slots, the pressure cap is still fitted over the upper end of the inner core, and the protrusions are located within the slots.

15. The vertebral body distraction tool according to claim 6, wherein a second stop step is formed on an outer cylinder wall of the outer sleeve, and a lower end of the lower cylinder abuts against the second stop step.

16. The vertebral body distraction tool according to claim 15, wherein the upper end of the inner core is of a prismatic structure; the pressure cap is of a cylindrical structure; a cavity of the pressure cap has a prismatic shape mating with the upper end of the inner core; the pressure cap is fitted over the upper end of the inner core; engagement blocks are fixed on an outer cylinder wall of the pressure cap; engagement slots are axially arranged on an inner cylinder wall of the upper cylinder; the engagement blocks are located within the engagement slots; the engagement blocks slide along the engagement slots; and when the pressure cap slides up along the axial direction of the upper tool cap to release the engagement blocks from the engagement slots, the pressure cap is still fitted over the upper end of the inner core.

17. The vertebral body distraction tool according to claim 15, wherein an outer side wall of the upper end of the inner core is provided with protrusions arranged axially; slots arranged axially are provided in a cavity of the pressure cap; the pressure cap is fitted over the upper end of the inner core; the protrusions are located within the slots; the protrusions slide along the slots; engagement blocks are fixed on an outer cylinder wall of the pressure cap; engagement slots are axially arranged on an inner cylinder wall of the upper cylinder; the engagement blocks are located within the engagement slots; the engagement blocks slide along the engagement slots; and when the pressure cap slides up along the axial direction of the upper tool cap to release the engagement blocks from the engagement slots, the pressure cap is still fitted over the upper end of the inner core, and the protrusions are located within the slots.

18. The vertebral body distraction tool according to claim 15, wherein an outer side wall of the upper end of the inner core is provided with slots arranged axially; protrusions arranged axially are provided in a cavity of the pressure cap; the pressure cap is fitted over the upper end of the inner core; the protrusions are located within the slots; the protrusions slide along the slots; engagement blocks are fixed on an outer cylinder wall of the pressure cap; engagement slots are axially arranged on an inner cylinder wall of the upper cylinder; the engagement blocks are located within the engagement slots; the engagement blocks slide along the engagement slots; and when the pressure cap slides up along the axial direction of the upper tool cap to release the engagement blocks from the engagement slots, the pressure cap is still fitted over the upper end of the inner core, and the protrusions are located within the slots.

* * * * *